(12) United States Patent
Chun et al.

(10) Patent No.: US 9,068,231 B2
(45) Date of Patent: Jun. 30, 2015

(54) METHOD FOR SCREENING CANCER THERAPEUTIC AGENT USING GALECTIN-3, GSK-3β, AND FASCIN-1

(75) Inventors: Kyung-Hee Chun, Seoul (KR); Seok-Jun Kim, Bucheon-si (KR); Teak-Chin Cheong, Seoul (KR); Il-Ju Choi, Seoul (KR); Yeon Su Lee, Goyang-si (KR); Sang-Jin Lee, Goyang-si (KR)

(73) Assignee: National Cancer Center, Goyang-si (KR)

( * ) Notice: Subject to any disclaimer, the term of this patent is extended or adjusted under 35 U.S.C. 154(b) by 273 days.

(21) Appl. No.: 12/901,337

(22) Filed: Oct. 8, 2010

(65) Prior Publication Data

US 2011/0250584 A1    Oct. 13, 2011

(30) Foreign Application Priority Data

Apr. 7, 2010 (KR) .................. 10-2010-0031985

(51) Int. Cl.
| | |
|---|---|
| *C12Q 1/00* | (2006.01) |
| *C12Q 1/68* | (2006.01) |
| *G01N 33/53* | (2006.01) |
| *G01N 33/50* | (2006.01) |
| *G01N 33/68* | (2006.01) |

(52) U.S. Cl.
CPC .......... *C12Q 1/6886* (2013.01); *G01N 33/6845* (2013.01); *G01N 2500/04* (2013.01); *G01N 2500/02* (2013.01); *C12Q 2600/136* (2013.01); *G01N 33/5011* (2013.01); *G01N 2333/4724* (2013.01); *G01N 2333/9121* (2013.01); *G01N 2440/14* (2013.01)

(58) Field of Classification Search
CPC .......... G01N 2500/02; G01N 2500/04; G01N 2500/10
See application file for complete search history.

(56) References Cited

FOREIGN PATENT DOCUMENTS

| | | |
|---|---|---|
| EP | 1845094 A1 * | 10/2007 |
| WO | 2006-073202 A1 | 7/2006 |

OTHER PUBLICATIONS

Kim et al., Gastroenterology, 2010, 138(3): 1035-1045, Epub Oct. 8, 2009.*
Shimura et al., Cancer Res., 2005, 65(9): 3535-3537.*
Vignjevic et al., Cancer Res. 2007, 67(14): 6844-6853.*
Izquierdo, Cancer Gene Therapy, 12: 217-227, 2005.*
Shankar, JAMA, 293(11), 1367-73, 2005.*
Heidenreich, Current Pharmaceutical biotechnology 5: 349-354, 2004.*
Shumei Song et al., "Galectin-3 Mediates Nuclear β-Catenin Accumulation and Wnt Signaling in Human Colon Cancer Cells by Regulation of Glycogen Synthase Kinase-3β Activity", Cancer Research, Feb. 3, 2009, 69(4), pp. 1343-1349.
Su-Feng Chen et al., "Effects of small interfering RNAs targeting Fascin on gene expression in oral cancer cells", Journal of Oral Pathology and Medicine, 2009, 38(9), pp. 722-730.
Liang et al., "In vitro scratch assay: a convenient and inexpensive method for analysis of cell migration in vitro," *Nature Protocols* 2(2): 329-333, 2007.
Woo, "Secretion of Macrophage Differentiation Antigen, Mac-2," *Korean J. of Immunology* 15(1): 61-68, Apr. 1993.
Jope et al., "Glycogen Synthase Kinase-3 (GSK3): Inflammation, Diseases, and Therapeutics," *Neurochem Res.* 32(4-5): 577-595, 2007.

* cited by examiner

*Primary Examiner* — Hong Sang
(74) *Attorney, Agent, or Firm* — Seed IP Law Group PLLC

(57) ABSTRACT

Disclosed is a method for screening a novel cancer therapeutic agent. The cancer therapeutic agent exhibits down-regulation of galectin-3 and fascin-1 or interferes with the interaction between galectin-3 and GSK-3β.

5 Claims, 10 Drawing Sheets

SEQUENCE LISTING

```
<160> NUMBER OF SEQ ID NOS: 24

<210> SEQ ID NO 1
<211> LENGTH: 25
<212> TYPE: RNA
<213> ORGANISM: Artificial Sequence
<220> FEATURE:
<223> OTHER INFORMATION: siRNA for Galectin-3

<400> SEQUENCE: 1
auaugaagca cuggugaggu cuaug                                               25

<210> SEQ ID NO 2
<211> LENGTH: 22
<212> TYPE: RNA
<213> ORGANISM: Artificial Sequence
<220> FEATURE:
<223> OTHER INFORMATION: siRNA for fascin-1
```

```
<400> SEQUENCE: 2
uccagcaaga augccagcug cu                                              22

<210> SEQ ID NO 3
<211> LENGTH: 20
<212> TYPE: DNA
<213> ORGANISM: Artificial Sequence
<220> FEATURE:
<223> OTHER INFORMATION: Forward primer for FSCN1

<400> SEQUENCE: 3
acctgtctgc caatcaggac                                                 20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for FSCN1

<400> SEQUENCE: 4
cccattcttc ttggaggtca                                                 20

<210> SEQ ID NO 5
<211> LENGTH: 22
<212> TYPE: DNA
<213> ORGANISM: Artificial Sequence
<220> FEATURE:
<223> OTHER INFORMATION: Forward primer for LGAL3

<400> SEQUENCE: 5
atggcagaca atttttcgct cc                                              22

<210> SEQ ID NO 6
<211> LENGTH: 22
<212> TYPE: DNA
<213> ORGANISM: Artificial Sequence
<220> FEATURE:
<223> OTHER INFORMATION: Reverse primer for LGAL3

<400> SEQUENCE: 6
atgtcaccag aaattcccag tt                                              22

<210> SEQ ID NO 7
<211> LENGTH: 17
<212> TYPE: DNA
<213> ORGANISM: Artificial Sequence
<220> FEATURE:
<223> OTHER INFORMATION: Forward primer for beta-actin

<400> SEQUENCE: 7
agcctcgcct ttgccga                                                    17

<210> SEQ ID NO 8
<211> LENGTH: 15
<212> TYPE: DNA
<213> ORGANISM: Artificial Sequence
<220> FEATURE:
<223> OTHER INFORMATION: Reverse primer for beta-actin

<400> SEQUENCE: 8
ctggtgcctg gggcg                                                      15

<210> SEQ ID NO 9
```

```
<211> LENGTH: 20
<212> TYPE: DNA
<213> ORGANISM: Artificial Sequence
<220> FEATURE:
<223> OTHER INFORMATION: Forward primer for GAPDH

<400> SEQUENCE: 9
ggctgctttt aactctggta                                              20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for GAPDH

<400> SEQUENCE: 10
acttgatttt ggagggatct                                              20

<210> SEQ ID NO 11
<211> LENGTH: 20
<212> TYPE: DNA
<213> ORGANISM: Artificial Sequence
<220> FEATURE:
<223> OTHER INFORMATION: Forward primer for fascin-1 promoter

<400> SEQUENCE: 11
aatgtccagg aaaagcctca                                              20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for fascin-1 promoter

<400> SEQUENCE: 12
cccaatttca tgggactctg                                              20

<210> SEQ ID NO 13
<211> LENGTH: 20
<212> TYPE: DNA
<213> ORGANISM: Artificial Sequence
<220> FEATURE:
<223> OTHER INFORMATION: Forward primer pcDNA3.1-NT-GFP-gal3 for Gal-3
      expression gene

<400> SEQUENCE: 13
atggcagaca atttttcgct                                              20

<210> SEQ ID NO 14
<211> LENGTH: 27
<212> TYPE: DNA
<213> ORGANISM: Artificial Sequence
<220> FEATURE:
<223> OTHER INFORMATION: Reverse primer pcDNA3.1-NT-GFP-gal3 for Gal-3
      expression gene

<400> SEQUENCE: 14
ttatatcatg gtatatgaag cactggt                                      27

<210> SEQ ID NO 15
<211> LENGTH: 27
<212> TYPE: DNA
<213> ORGANISM: Artificial Sequence
<220> FEATURE:
<223> OTHER INFORMATION: Forward primer for human galectin-3 gene
```

```
<400> SEQUENCE: 15
ggatccatgg cagacaattt ttcgctc                                       27

<210> SEQ ID NO 16
<211> LENGTH: 26
<212> TYPE: DNA
<213> ORGANISM: Artificial Sequence
<220> FEATURE:
<223> OTHER INFORMATION: Reverse primer for human galectin-3 gene

<400> SEQUENCE: 16
tcgagttata tcatggtata tgaagc                                        26

<210> SEQ ID NO 17
<211> LENGTH: 27
<212> TYPE: DNA
<213> ORGANISM: Artificial Sequence
<220> FEATURE:
<223> OTHER INFORMATION: Forward primer for Galectin-3 S96A 1

<400> SEQUENCE: 17
ggatccatgg cagacaattt ttcgctc                                       27

<210> SEQ ID NO 18
<211> LENGTH: 35
<212> TYPE: DNA
<213> ORGANISM: Artificial Sequence
<220> FEATURE:
<223> OTHER INFORMATION: Reverse primer for Galectin-3 S96A 1

<400> SEQUENCE: 18
gacagccagc agccaccgga gcctcacctg ccact                              35

<210> SEQ ID NO 19
<211> LENGTH: 36
<212> TYPE: DNA
<213> ORGANISM: Artificial Sequence
<220> FEATURE:
<223> OTHER INFORMATION: Reverse primer for Galectin-3 S96A 2

<400> SEQUENCE: 19
tccggtggct gctggctgtc cagaagatgg gtaggc                             36

<210> SEQ ID NO 20
<211> LENGTH: 27
<212> TYPE: DNA
<213> ORGANISM: Artificial Sequence
<220> FEATURE:
<223> OTHER INFORMATION: Reverse primer for Galectin-3 S96A 2

<400> SEQUENCE: 20
ctcgagttat atcatggtat atgaagc                                       27

<210> SEQ ID NO 21
<211> LENGTH: 250
<212> TYPE: PRT
<213> ORGANISM: Homo sapiens
<220> FEATURE:
<221> NAME/KEY: BINDING
<222> LOCATION: (92)..(96)
<223> OTHER INFORMATION: Amino acid sequence for galectin-3

<400> SEQUENCE: 21

Met Ala Asp Asn Phe Ser Leu His Asp Ala Leu Ser Gly Ser Gly Asn
 1               5                  10                  15
```

```
Pro Asn Pro Gln Gly Trp Pro Gly Ala Trp Gly Asn Gln Pro Ala Gly
                20                  25                  30
Ala Gly Gly Tyr Pro Gly Ala Ser Tyr Pro Gly Ala Tyr Pro Gly Gln
            35                  40                  45
Ala Pro Pro Gly Ala Tyr Pro Gly Gln Ala Pro Pro Gly Ala Tyr Pro
        50                  55                  60
Gly Ala Pro Gly Ala Tyr Pro Gly Ala Pro Gly Val Tyr Pro
65                  70                  75                  80
Gly Pro Pro Ser Gly Pro Gly Ala Tyr Pro Ser Ser Gly Gln Pro Ser
                85                  90                  95
Ala Thr Gly Ala Tyr Pro Ala Thr Gly Pro Tyr Gly Ala Pro Ala Gly
                100                 105                 110
Pro Leu Ile Val Pro Tyr Asn Leu Pro Leu Pro Gly Gly Val Val Pro
                115                 120                 125
Arg Met Leu Ile Thr Ile Leu Gly Thr Val Lys Pro Asn Ala Asn Arg
130                 135                 140
Ile Ala Leu Asp Phe Gln Arg Gly Asn Asp Val Ala Phe His Phe Asn
145                 150                 155                 160
Pro Arg Phe Asn Glu Asn Asn Arg Arg Val Ile Val Cys Asn Thr Lys
                165                 170                 175
Leu Asp Asn Asn Trp Gly Arg Glu Glu Arg Gln Ser Val Phe Pro Phe
                180                 185                 190
Glu Ser Gly Lys Pro Phe Lys Ile Gln Val Leu Val Glu Pro Asp His
                195                 200                 205
Phe Lys Val Ala Val Asn Asp Ala His Leu Leu Gln Tyr Asn His Arg
210                 215                 220
Val Lys Lys Leu Asn Glu Ile Ser Lys Leu Gly Ile Ser Gly Asp Ile
225                 230                 235                 240
Asp Leu Thr Ser Ala Ser Tyr Thr Met Ile
                245                 250

<210> SEQ ID NO 22
<211> LENGTH: 5
<212> TYPE: PRT
<213> ORGANISM: Homo sapiens

<400> SEQUENCE: 22

Ser Gly Gln Pro Ser
  1               5

<210> SEQ ID NO 23
<211> LENGTH: 9
<212> TYPE: PRT
<213> ORGANISM: Homo sapiens

<400> SEQUENCE: 23

Asn His Arg Val Lys Lys Leu Asn Glu
  1               5

<210> SEQ ID NO 24
<211> LENGTH: 7
<212> TYPE: DNA
<213> ORGANISM: Homo sapiens

<400> SEQUENCE: 24 ctttgat                                                         7
```

METHOD FOR SCREENING CANCER THERAPEUTIC AGENT USING GALECTIN-3, GSK-3β, AND FASCIN-1

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690156_405_SEQUENCE_LISTING.txt. The text file is 7.2 KB, was created on Jan. 5, 2015, and is being submitted electronically via EFS-Web.

BACKGROUND OF THE INVENTION

1. Field of the Invention

The present invention relates to a novel cancer therapeutic agent and a method for screening for the same. More particularly, the present invention relates to a novel cancer therapeutic agent capable of interfering with the up-regulation of fascin-1 by galectin-3 or the interaction between galectin-3 and GSK-3β, and a method for screening for the same.

2. Description of the Related Art

Cancer is one of the most common causes of morbidity and mortality all over the world today. The incidence of cancer is expected to increase due to the increasing average life expectancy, with the onset age being lowered. The ACS's (American Cancer Society) annual Cancer Statistics article states that in 2007, 12 million or more new cancer cases were diagnosed worldwide, with a death toll of about 7.6 million cancer patients which is a fatality rate of about twenty thousand per day.

In South Korea, cancer (malignant neoplasm) is responsible for the death of 62,887 persons per, which corresponds to 25.5% (29.6% for men and 20.5% for women) of the total death toll of 246,515 persons (death rate 512 per hundred thousands of the population) in 2002, ranking it first amongst the causes of death. Lung cancer, breast cancer, hepatic cancer, colorectal cancer, and pancreatic cancer are in decreasing order the cancer with the highest mortality, accounting for around 70% of total cancer deaths. Lung cancer, gastric cancer, hepatic cancer and colorectal cancer are the leading causes of cancer death in males, accounting for 28,147 deaths in that period (around 70% of all cancer deaths (40,177)). For women, 13,630 deaths, which were around 60% of the total cancer deaths in that period (22,710), were caused by the five cancers of gastric cancer, lung cancer, hepatic cancer, colon cancer and pancreatic cancer.

An analysis report has it that the death rate from gastric cancer has gradually decreased from 24% to 16% over the 10 years between 1996 and 2006.

Although decreasing, the death rate of gastric cancer is significant, and gastric cancer still remains as one of the three leading cancers in South Korea.

When affected by gastric cancer, patients feel a variety of symptoms ranging from no pain to extremely severe pain. In addition, the symptoms of gastric cancer are not peculiar, but resemble general gastrointestinal symptoms. In fact, most patients in the early stage of gastric cancer live without feeling any symptoms. If any, the symptoms of early gastric cancer are so insignificant that they are likely to be neglected by most patients, which contributes to an increase in the mortality rate of gastric cancer.

The best therapy for gastric cancer which has been identified thus far is gastrectomy. That is, the resection of the lesion is the only way to completely heal gastric cancer. Many operative processes may be provided for gastrectomy. Once it has been determined that a surgery would be able to completely heal gastric cancer, a surgical operation is preferably performed wherein as wide a region as possible including the lesion is resected. However, the resection area must be limited in consideration of the sequela of the resection. If the target of the gastrectomy includes neighboring organs such as lymph glands, satisfactory convalescence may be not given to the patients. Upon the metastasis of gastric cancer to other organs, a surgical operation is not a therapy that can offer complete healing. In this regard, alternative therapies such as chemotherapy are taken. Most of the currently used anticancer agents are useful, but temporally, for relieving symptoms or restraining post-operative recurrence and extending the duration of life. However, the administration of anticancer agents imparts the patients with the dual burdens of side effects and financial loss. Therefore, there is a desperate need for a novel cancer therapeutic agent and a method for developing the same.

In association with the progress of gastric cancer, galectins vary in expression level with progression into malignant or benign tumors. Galectins are specific carbohydrate-binding proteins which are widely distributed in humans and animals. Despite having obtained knowledge about the biochemical and microbiological properties of galetins, the exact functions thereof remain controversial. Starting from galectin-1, the members of the galectin family exist as monomers or dimers with molecular weights of 14-36 kDa. Galetin-1, -2, -3, -7 and -8 are known to be involved in the regulation of fetal development and cell growth, attachment and tumorigenesis. Some of the galectin members are distributed primarily on specific organs or cells: galectin-2 is confined specifically to hepatic cancer cells, galectin-4 to the epithelial cells of the gastrointestinal tract, galectin-5 to erythrocytes, and galectin-7 to keratinocytes of the squamous epithelium.

Galectin-3, one of the most studied members of the galectin family, also called CBP-35, Mac-2, εBP, RL-29, L-35 or L-31, having a molecular weight of 26,200-32,300, is implicated in the growth, differentiation and tumorigenesis of cells, fetal development and IgE-mediated allergic responses, and plays an important role in intercellular or cell-matrix binding. Also, galectin-3 is distributed over a wide range of cells including leukocytes, dendritic cells of lymphatic organs, Langerhan's cells, and the epithelial cells of the intestinal mucosa and renal tubules. Particularly, galectin-3 is barely detected in the intestinal crypt epithelium, but increases in expression level with the progression of cell differentiation, suggesting that galectin-3 plays a role in cell development and differentiation. New members of the galectin family continue to be found and 9 have been found thus far. In addition, galectins have in common with interleukin-1 or fibroblast growth factors the fact that they lack signal sequences during expression although they are extracellular proteins.

In contrast to general soluble proteins, galectin-3 can be extracellularly secreted without signal peptides (Woo, H. J., Secretion of macrophage differentiation antigen, Mac-2, 15: 61-68, 1993). It has been anticipated that the analysis of the mechanism of galectin functions at molecular levels would provides a basis for the diagnosis, prevention and treatment of inflammatory diseases such as cancer and arthritis. In fact, a research report states that the expression of galectin-3 is correlated with the generation of carcinoma. However, no reports have disclosed that cancer or inflammatory diseases can be treated by suppressing the expression of galectin-3.

Further, nowhere has the mechanism of galectin-3 been reported in previous documents.

SUMMARY OF THE INVENTION

Leading to the present invention, intensive and thorough research into the development of novel chemotherapeutic agents and screening techniques therefor, conducted by the present inventors, resulted in the finding that when the expression or activity of galectin-3, a β-galactoside-binding protein that increases gastric cancer cell motility in response to integrin signaling, is decreased or reduced, a restricted change in morphology and a decrease in fascin-1 expression level, motility and metastasis were detected in the gastric cancer cells and were closely correlated with interaction between galectin-3 and GSK-3β, so that the agent can be useful as a cancer therapeutic agent which functions to reduce the motility of gastric cancer cells and the metastatic effects of malignant tumor cells.

It is therefore an object of the present invention to provide a method for screening a cancer therapeutic agent, comprising: a) treating cancer cells with a candidate for chemotherapy; b) determining phosphorylation of GSK-3β (glycogen synthetase kinase-3β) and an expression level of fascin-1 in the treated cells; and c) comparing the phosphorylation of GSK-3β and the expression level of fascin-1 between the treated cells and a control.

It is another object of the present invention to provide a cancer therapeutic composition, comprising as an active ingredient a material capable of interfering with the interaction between galectin-3 and GSK-3β.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

In accordance with an aspect thereof, the present invention pertains to a method for screening for a cancer therapeutic agent, comprising: a) treating cancer cells with a candidate for chemotherapeutic agents; b) analyzing the treated cancer cells for GSK-3β(glycogen synthetase kinase-3β) phosphorylation and Fascin-1 expression level; and c) comparing the GSK-3β phosphorylation and Fascin-1 expression level between the treated cell and a control.

By the screening method, when the phosphorylation of GSK-3β and the expression level of Fascin-1 in the treated cells are found to decrease in comparison with the control, the candidate can be determined to be useful as a cancer therapeutic agent. An equal or increased level of GSK-3β phosphorylation or Fascin-1 expression in comparison with the control provides a basis for determining the candidate as being unsuitable as a cancer therapeutic agent.

In a preferred embodiment, the method for screening for a cancer therapeutic agent may further comprise comparing the expression level of galectin-3 or GSK-3β between the candidate and the control. When the candidate causes the expression level of galectin-3 or GSK-3β to decrease compared to the control, it can be determined as a cancer therapeutic agent. When causing an equal or increased expression level of galectin-3 or GSK-3β, the candidate is determined to not be a cancer therapeutic agent.

Figure 2:
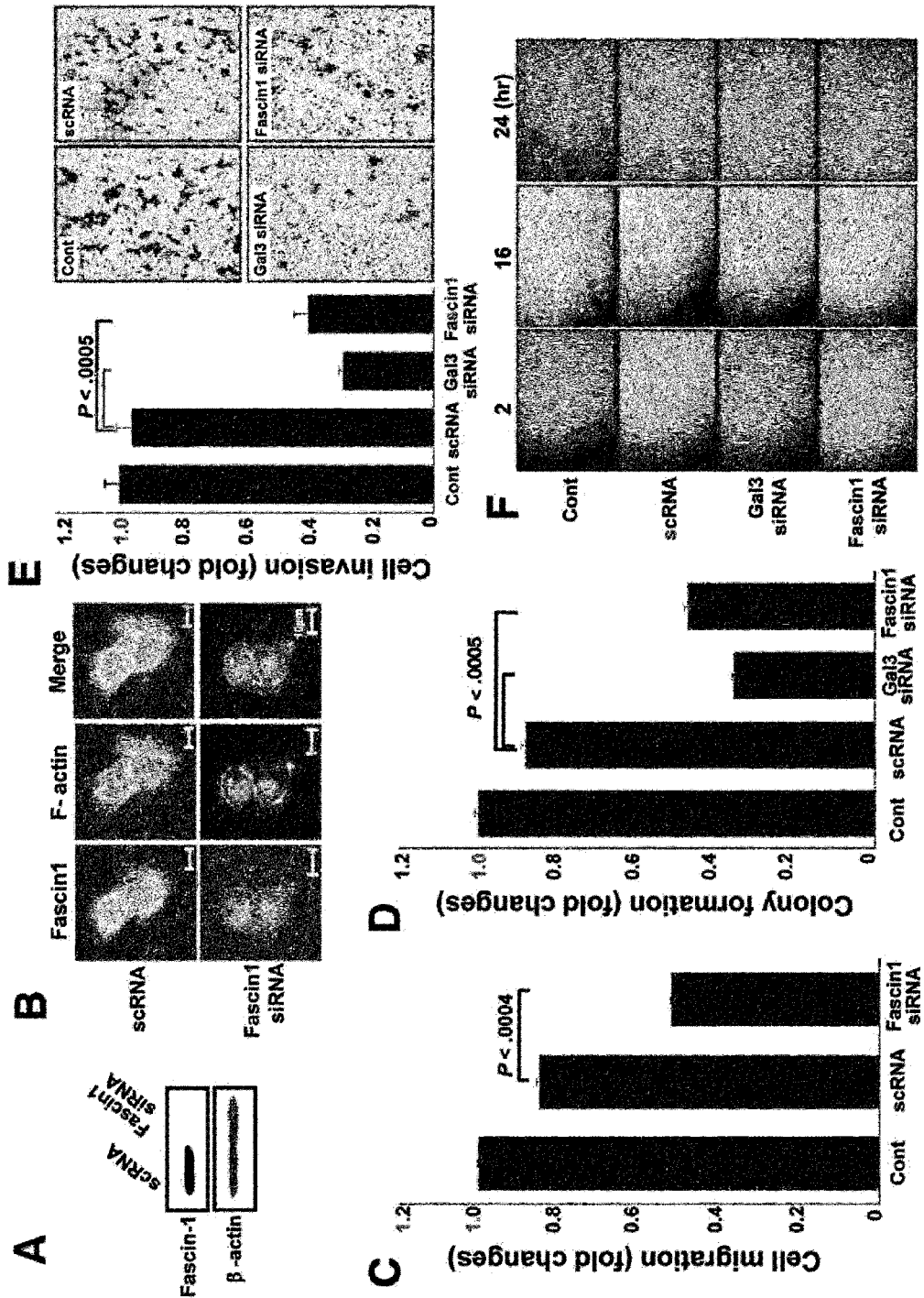
FIG. 2 shows the effect of fascin-1 silencing on the motility of human gastric cancer cells. (A) Fascin-1 protein expression in MKN-28 cells transfected with scrambled siRNA (scRNA) or fascin-1 siRNA. β-actin was used as a loading control. (B) Immunocytochemical analysis of MKN-28 cells transfected with scRNA or fascin-1 siRNA by DAPI (blue), anti-fascin-1 FITC (green) and anti-F-actin Texas Red (red) was conducted using confocal microscopy. Bars represent 10 µm in length. (C) Cell migration in fascin-1-silenced MKN-28 cells. Results of the migration assay are presented as a histogram, with statistical significance (P<0.0004). (D to E) (D) Colony formation assay, (E) invasion assay, and (F) wound healing assay of MKN-28 cells were performed with transfected galectin-3 and fascin-1 siRNAs. Results of the colony formation assay and invasion assay are shown as a histogram, with statistical significance (P<0.0005). Cell migration was measured by microscopy.
Figure 6:
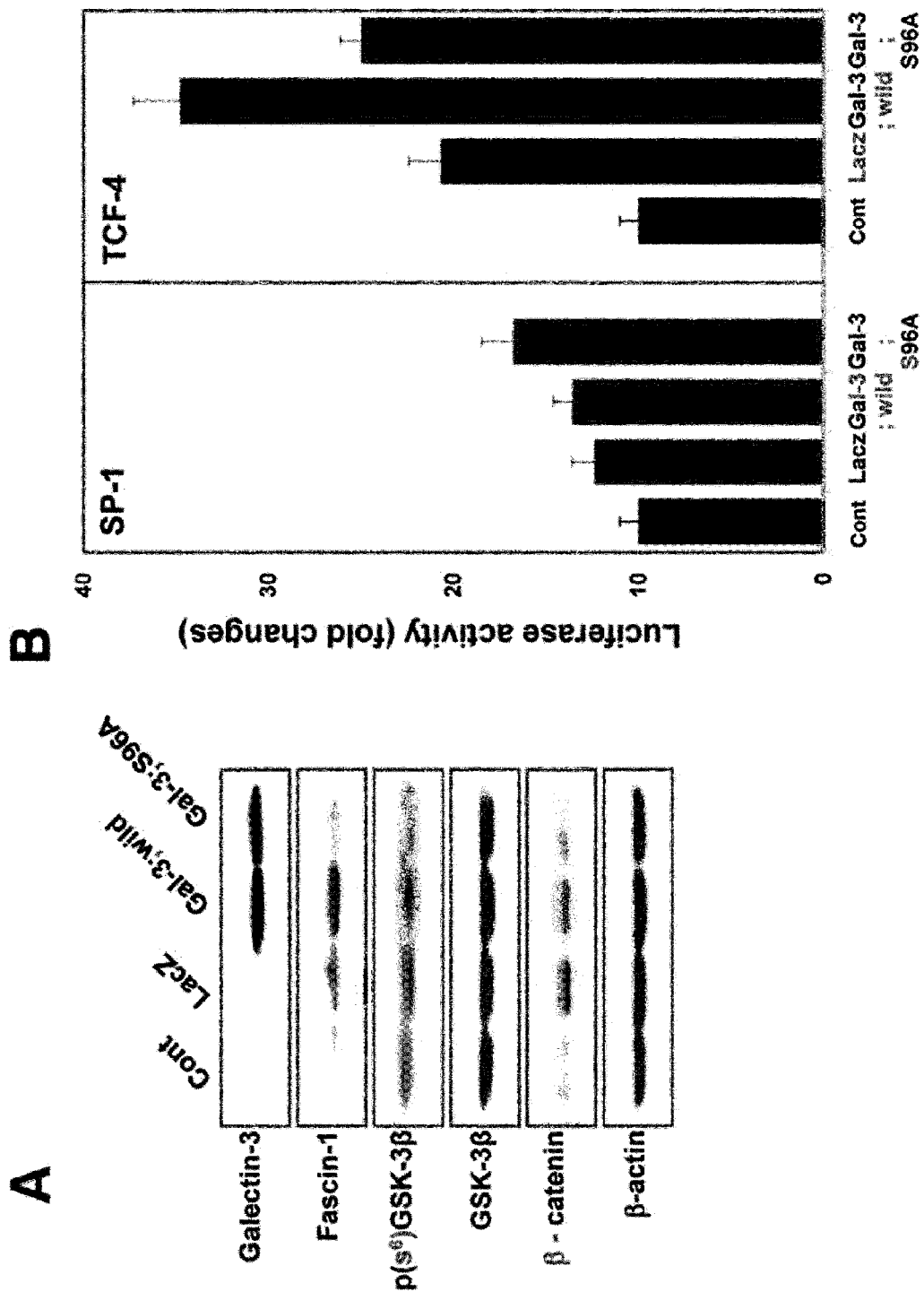
FIG. 6 shows the effect of galectin-3 mutation on fascin-1 expression in human gastric cancer SNU-638 cells infected with lenti-virus containing LacZ, galectin-3 (gal-3; wild-type), and serine 96 mutated galectin-3 (gal-3; S96A). (A) Expression levels of galectin-3, fascin-1, phosphorylated GSK-3β [pS$^6$] GSK-3β, and β-catenin as measured by Western blotting. β-actin was used as a loading control. (B) Luciferase activity of TCF4 in the cells. The construct of SP1 consensus was used as a negative control.

In an embodiment of the present invention, when cancer cells were treated with Fascin-1 siRNA, which is a candidate therapeutic agent, the cancer cells were observed to decrease in migration and invasion (FIG. 2). Upon treatment with galectin-3 mutated at amino acid 96, no effects were found on the phosphorylation of GSK-3β so that a decrease in the phosphorylation of GSK-3β occurred (FIG. 6), thus confirming that the mutation decreases the metastasis of gastric cancer cells by down-regulating fascin-1 expression.

Thus, substances which can interfere with the interaction of galectin-3 with GSK-3β or decrease the expression level of Fascin-1 or the phosphorylation of GSK-3β were identified as being useful as cancer therapeutic agents. In addition, whether these cancer therapeutic agents have an influence on interaction between galectin-3 and GSK-3β can be determined by the phosphorylation level of GSK-3β.

The term "GSK-3β (Glycogen synthase kinsase 3-β)", as used herein, is a serine/threonine protein kinase that mediates the addition of phosphate molecules on certain serine and threonine amino acids in particular cellular substrates. The phosphorylation of specific proteins by GSK-3 usually inhibits the substrate, as in the case of glycogen synthase and NFAT. In mammals, GSK-3 is encoded for by two known genes GSK-3α and GSK-3β. Being inhibited by the phosphorylation mediated by PI-3-kinase, GSK-3 proteins are known to play an important regulatory role in cell apoptosis.

The term "Fascin-1", as used herein, is a 55-kDa globular protein that aggregates F-actin into parallel bundles to rearrange the cytoskeleton and is one of the most highly conserved proteins. In vertebrates, the genome encodes three subtypes of the fascin family, including fascin-1, fascin-2, and fascin-3. The fascin family is of proteins principally expressed in the developing nervous system and mesoderm-derived tissues: fascin-1 is widely distributed over mesenchymal tissues and the nervous system, fascin-2 is expressed in retinal photoreceptor cells, and fascin-3 is testis specific.

Fascin, an actin cross-linking protein, has two actin-binding sites. The association of fascin with actin is inhibited when fascin is phosphorylated at serine 39 by protein kinase Cα(PKCα). Although the exact mechanism of the fascin phosphorylation at the serine residue still remains unknown, interaction between fascin and F-actin was found to be regulated by the condition of the extracellular matrix. The molecular basis for this regulation is attributed to thrombospondin-1 and fibronectin, depending on the activity of PKCα and GTPase.

As used herein, the term "galectin" means a 31 kDa protein which is a member of the beta-galactoside lectin family, characterized by the possession of carbohydrate-recognition-binding domains. Depending on the number and structure of the domains, galectin is classified into proto, chimera and tandem repeat types. There have been 14 galectins identified to date, which are known to be involved in various biological functions including embryonic development, cell adhesion, cell proliferation, apoptosis, mRNA splicing, etc.

The term "galectin-3", as used herein, is a unique chimera type of galectin proteins that is normally expressed in gastrointestinal, respiratory and renal epithelia as well as macrophages, eosinophils, neutrophils and mast cells. Galectin-3 is overexpressed in stomach carcinoma, pancreatic carcinoma, thyroid carcinoma, and colorectal carcinoma, but shows a decreased expression level in breast carcinoma and ovary carcinoma. The effect of galectin-3 on the prognosis of cancer varies depending on tumor types.

Galectin-3 is known to have various functions and exists primarily in the cytoplasm, but can be detected in the nucleus and extracellular matrix. Galectin-3 is structurally similar to bcl-2, but does not belong to the bcl-2 family. Both proteins have N-terminal regions rich in proline, glycine and alanine, and contain an asparagine-tryptophane-glycine-arginine motif at the C-terminus thereof. This motif, also called the "anti-apoptotic motif", is located in the BH-1 domain of Bcl-2, suggesting that galectin-3 functions, instead of or in mimicry of bcl-2, to inhibit the release of cytochrome C from the mitochondria thus to regulate apoptosis. In addition galectin-3 modulates cyclin and its inhibitors to arrest the cell cycle at late G1, thus preventing apoptosis. Inducing the apoptosis of NK cells and T lymphocytes that are implicated in the removal of tumor cells, galectin-3 in interstitial spaces has an indirect influence on the survival of tumor cells. Consequently, the expression of galectin-3 brings about negative effects on the prognosis of a tumor, which is consistent with the fact that while galectin is predominantly expressed in the nucleus in normal cells, the cytoplasmic expression thereof increases with oncogenesis. However, neither the expression of galectin nor the expression mechanism of genes downstream thereof has been known. In an embodiment of the present invention, a gastric cancer cell line with an increased expression level of galectin-3 was induced to suppress the expression of galectin-3 by using siRNA, after which it was monitored for morphogenesis, fascin-1 expression level, migration, and metastasis. In contrast to the overexpression of galectin-3, its decreased expression level was observed to lead to a decrease in the expression level of the actin-bundling protein fascin-1 and the intranuclear expression level of GSK-3β and β-catenin. Also, GSK-3β phosphorylation was decreased. Therefore, the treatment of cancer cells with a cancer therapeutic agent resulted in a decrease in the expression level of fascin-1 and the phosphorylation of GSK-3β, with the concomitant decrease of galectin-3, β-catenin and GSK-3β expression.

As used herein, the term "control" is intended to refer to a group or cell which is treated with a candidate for cancer therapy and is used for comparing the phosphorylation of GSK-3β and the expression levels of fascin-1, galectin-3, β-catenin and GSK-3β in cancer cells with a candidate for cancer therapy. The term "candidate", as used herein, is intended to refer to an agent to be tested for cancer therapeutic activity. The cancer therapeutic activity is determined by measuring the ability of the candidate to directly or indirectly modulate the phosphorylation of GSK-3β and the expression of fascin-1, galectin-3, β-catenin and GSK-3β. A wide spectrum of compounds including proteins, oligopeptides, small organic molecules, polysaccharides, polynucleotides, etc. may fall within the scope of the candidate of the present invention. The candidate may comprise synthetic materials as well as native materials.

The term "cancer therapeutic agent", as used herein, is intended to refer to a drug or a chemical agent which has a mechanism of destroying cancer cells. Most cancer therapeutic agents cause multiple injuries to cells and prevent cells from being further replicated. Preferably, the cancer therapeutic agents according to the present invention can function to suppress the metastasis and migration of cancer and, more preferably, gastric cancer.

According to the action mechanism, cancer therapeutic agents may be classified into alkylating agents, antimetabolites, plant alkylating agents, antibiotics, urea nitrate agents, enzymes, steroid agents, and immunotherapeutic agents. In detail, the anticancer activity of alkylating agents is based on the ability to interfere with the biosynthesis of DNA to suppress the growth of cancer cells and is characterized by cell-cycle specificity. Generally, alkylating agents inhibit the progression of cancer cells from the G1 phase to the S phase. Antimetabolites are similar in structure to the natural metabolites produced by the cells, but are not naturally occurring materials. They are known to allow the replication of cells, but destroy cell-specific functions, and act only on the S phase of the cell cycle. Plant alkylating agents interfere with the mitosis of cells to inhibit the growth of cancer cells. Antibiotics inhibit DNA synthesis to suppress the growth of cancer cells, thus exerting an influence on all phases of the cell cycle. Having an ability to pass through the brain-blood barrier, urea nitrate is not applied to children, except for the treatment of brain tumors.

For use as cancer therapeutic agents, the candidates, when administered, must decrease the expression level of galectin-3 and the phosphorylation of GSK-3β in the tumor suspected cells or tumor positive cells, compared to the control. Examples of the candidates useful in the present invention include antibodies, compounds, viruses, nucleic acid molecules, vectors carrying nucleic acid molecules, etc., but are not limited thereto. Preferably, the cancer therapeutic agent can recognize the phosphorylation of GSK-3β. So long as it inhibits interaction between galectin-3 and GSK-3β, any material may be used as a cancer therapeutic candidate.

As used herein, the term "antibodies" refers to globulin proteins that respond to foreign objects while circulating in the body along with blood and lymph fluids. Antibodies, also called immunoglobulins, are proteins secreted into the bodily fluids from B cells and specifically react with respective antigens. One antibody molecule consists of two heavy chains and two light chains. Each chain has a variable region at the N-terminus thereof. Each variable region is composed of three complementary determining regions (CRDs) and four framework regions (FRs). CDRs determine antigen-binding specificity and exist as relatively short peptide sequences supported within the variable domains by conserved framework regions.

Preferably, the antibodies useful in the present invention recognize a GSK-3β that has been phosphorylated and that inhibits the interaction between galectin-3 and GSK-3β, to thereby suppress the expression of fascin-1 which interacts with them.

The term "siRNA", as used herein, refers to a short double-stranded RNA molecule 20-25 nucleotides long, which is produced as a result of processing by dicer. It shows complementarity base pair interactions with a target mRNA to interfere with the expression of the protein of interest. Complementarity between siRNA 21-25 long and a target mRNA determines the ability of the siRNA to induce the target mRNA to undergo degradation or to prevent the target mRNA from being translated. Preferably, an antibody recognizing the phosphorylation of GSK-3β can be applied to the treatment of a subject suspected of having a tumor or a subject who has tested positive for a tumor. In this context, when the phosphorylation of GSK-3β decreases, TCF-4 decreases in activity, which in turn induces a decrease in the expression level of β-catenin, thus decreasing the expression level of the complex molecules which induce the expression of fascin-1. As a result, fascin-1 decreases in expression level, thus suppressing the migration of tumor cells. For use as cancer therapeutic agents, nucleic acid molecules are antisense oligonucleotides or siRNAs which interfere with the transcription of galectin-3. Taking advantage of their complementarity with target genes, these nucleic acid molecules can be used to effectively inhibit complexes responsible for the expression of fascin-1 that is directly involved in the proliferation, differentiation and migration of tumor cells.

The phosphorylation of GSK-3β and the expression level of fascin-1 in cancer cells can be determined by analyzing the antigen-antibody reaction in which an antibody interfering with interaction between galectin-3 and GSK-3β reacts with an antibody specific for the complementary region of the antibody. As used herein, the term "antigen-antibody reaction" refers to the reaction of galectin-3 or GSK-3β of a tumor-suspected or tumor-positive subject with an antibody specific therefor. The antigen-antibody reaction can be quantitatively determined by measuring the size of the signal generated by the detection label.

Such a detection label may be selected from a group consisting of enzymes, fluorescent substances, ligands, luminescent substances, microparticles, redox molecules and radioactive isotopes, but the present invention is not limited to these examples. Examples of the enzymes useful as detection labels include β-glucuronidase, β-D-glucosidase, β-D-galactosidase, urease, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphoenolpyruvate decarboxylase, and β-lactamase, but are not limited thereto. Examples of the fluorescent substances useful as detection labels include fluorescein, isothiocyanate, rhodamine, phycoerythrine, phycocyanin, alophycocyanin, O-phthalaldehyde, and fluorescamine, but are not limited thereto. Illustrative, non-limiting examples of the ligands useful as detection labels include biotin derivatives. Examples of the luminescent substances useful as detection labels include acridinium ester, luciferin, and luciferase, but not limited thereto. Examples of the microparticles useful as detection labels include colloidal gold, and colored latex, but are not limited thereto. Examples of the redox molecules useful as detection labels include ferrocene, ruthenium complex, viologen, quinine, Ti ion, Cs ion, diimide, 1,4-benzoquinone, hydroquinone, $K_4 W(CN)_8$, $[Os (bpy)_3]^{2+}$, $[RU(bpy)_3]^{2+}$, and $[MO(CN)_8]^{4-}$, but are not limited thereto. Examples of the radioactive isotopes useful as detection labels include, but are not limited to, $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

In addition, the expression level of a fascin-1 gene that is involved in the proliferation, differentiation and motility of tumor cells can be determined by measuring mRNA or protein levels of the fascin-1 gene. As long as it can determine the expression level of fascin-1, any method may be used in the present invention. Examples include Western blotting, ELISA, radioimmunoassay, radioimmunodiffusion, Ouchterlony immunodiffusion, rocket immunoelectrophoresis, immunohistostaining assay, immunoprecipitation assay, complement fixation assay, FACS, and protein chips, but are not limited thereto.

The expression of galectin-3 or the phosphorylation of GSK-3β can be determined by measuring the level of galectin-3 mRNA or protein or phosphorylated GSK-3β, as described above.

A candidate is a material which is anticipated to have a therapeutic effect on cancer or tumors. As long as it is anticipated to directly or indirectly ameliorate or improve cancer or tumors, any material may be used as a candidate. Anticipatable materials include compounds, genes and proteins all of which fall within the scope of what makes a candidate.

In the screening method of the present invention, when the expression levels of galectin-3 and fascin-1 and the phosphorylation of GSK-3β obtained after the administration of a candidate are decreased compared to those obtained before the administration, the candidate may be determined to be a therapeutic agent for cancer or tumors. In accordance with an embodiment of the present invention, after a small interfering (si) RNA and a lentivirus vector were used to suppress the expression of galectin-3 in a human gastric cancer cell line, the expression level of the fascin-1 protein that is involved in the motility of gastric cancer cells was decreased. A decreased expression level of the actin-bundling protein fascin-1 was observed to be associated with the inhibition of motility and metastasis of gastric cancer cells, resulting in a therapeutic effect on cancer.

In accordance with another aspect thereof, the present invention pertains to a chemotherapeutic composition comprising a material interfering with the interaction between galectin-3 and GSK-3β.

Figure 8:
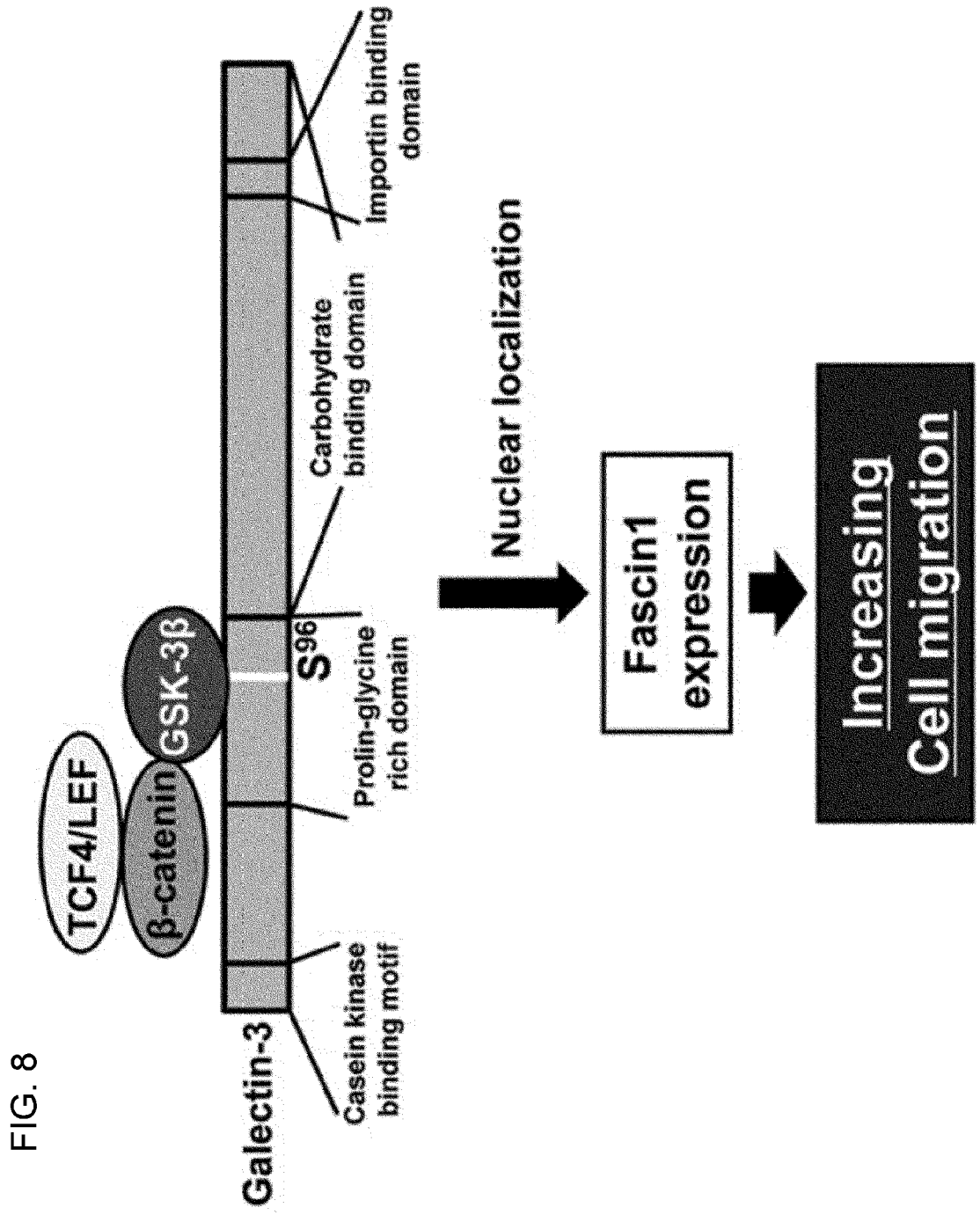
FIG. 8 is a schematic model for galectin-3-mediated enhancement of cell migration by the up-regulation of fascin-1. Galactin-3 interacts with GSK-3β directly, and the galectin-3, GSK-3β and β-catenin/TCF-4 complex translocates from the cytosol to the nucleus. This complex binds to a fascin-1 promoter and increases fascin-1 expression, thereby enhancing cell migration.
Figure 10:
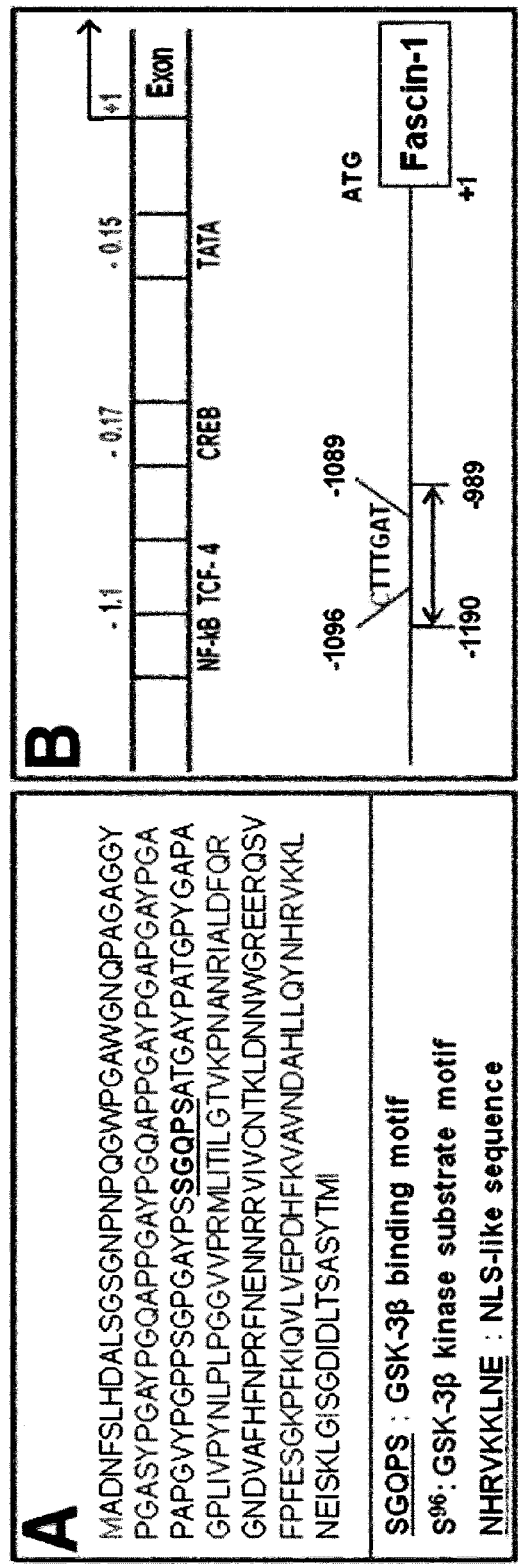
FIG. 10 shows an amino acid sequence of galectin-3 (SEQ ID NO. 21) and TCF-4 binding site on fascin-1 promoter. (A) The SGQPS (SEQ ID NO. 22) sequence of galectin-3, showing serine 96 as a kinase substrate motif of GSK-3β on galectin-3, which also has NLS (nuclear location sequence) NHRVKKLNE (SEQ ID NO. 23). (B) A schematic model of fascin-1 promoter interaction with TCF-4 binding site. The fascin-1 promoter contains a transcription factor binding site, such as NF-kB, CREB, and TCF-4 (upper). Primers for ChIP assay were prepared for the detection of a TCF-4 binding site (−1089~−1096, SEQ ID NO. 24) extending from −989 to −1190.

As described above, we first reported that galectin-3 binds directly to GSK-3β and promotes interaction between β-catenin and TCF-4 to increase the expression of fascin-1, resulting in facilitating the migration of cancer cells, that is, the metastasis of cancer. Further, we found that serine residues at positions 92 and 96 of galectin-3 are essential for the motif responsible for direct interaction with GSK-3β (FIGS. 8 and 10). Hence, the interference of galectin-3's binding to GSK-3β results in the inhibition of cancer metastasis, thus exhibiting a therapeutic effect on cancer. If they are designed to target binding sites of galectin-3 and GSK-3β to inhibit the interaction therebetween, which can be readily conducted by a practitioner of the art, siRNAs, antisense oligonucleotides, aptamers or antibodies can be used as cancer therapeutic agents.

In a preferred embodiment, the materials which can interfere with the binding of galectin-3 to GSK-3β may be in the form of compounds, nucleic acid molecules, peptides, viruses or vectors carrying the nucleic acid molecules. Examples include siRNAs, antisense oligonucleotides, aptamers and antibodies. Preferably, a material that interferes with the binding of galectin-3 to GSK-3β may target serine residues at positions 92 and 96 in the amino acid sequence of galectin-3 of SEQ ID NO. 21. The serine residues were first found to be constituents of the motif of galectin-3 responsible for interaction with GSK-3β (FIG. 10). The binding motif can be expressed as the "SGQPS (serine, glycine, glutamine, proline and serine)" motif (SEQ ID NO. 22). Preferably, the material that interferes with the binding of galectin-3 to GSK-3β may be a virus or vector carrying a nucleic acid molecule which codes for the amino acid residues at positions 92 to 96 of SEQ ID NO. 21. The terms "siRNA", "antisense", "oligonucleotide", "antibodies", and "virus or vector carrying a nucleic acid molecule" are as defined above. It should be understood that those skilled in the art can readily design an inhibitory substance targeting the binding motif between galectin-3 and GSK-3β, which has been first found by the present inventors, on the basis of molecular biological techniques.

As used herein, the term "aptamer" refers to a single-stranded oligonucleotide, 20-60 nt in length, which has activity when binding to a specific target molecule. Aptamers can adopt various three-dimensional conformations according to their sequences, showing high affinity for specific materials like antigen-antibody reaction. Aptamers can inhibit the activity of target molecules by binding with them. The aptamers useful in the present invention may be selected from among RNA, DNA, modified nucleic acid molecules and a combination thereof and may be in the form of linear chains or loops.

A better understanding of the present invention may be obtained through the following examples which are set forth to illustrate, but are not to be construed as limiting the present invention.

Example 1

Materials and Methods

<1-1> Cell Culture and Transfection

Human stomach cell lines were purchased from the Korean Cell Line Bank and maintained in RPMI 1604 supplemented with 5% fetal bovine serum (FBS) and 1% antibiotics. Galectin-3 and fascin-1 siRNAs (galectin-3 siRNA 5'-AUAUGAAGCACUGGUGAGGUCUAUG-3', SEQ ID NO. 1; and fascin-1 siRNA 5'-UCCAGCAAGAAUGCCAGCUGCU ACU-3', SEQ ID NO. 2) were obtained from Invitrogen and transfected transiently into cells using Lipofectamine RNAiMAX (Invitrogen) according to the manufacturer's instruction. 2 days after the transfection, the cells were harvested.

<1-2> RNA Isolation and Reverse Transcription PCR

Total RNA was isolated from malignant and normal gastric tissues of gastric cancer patients in the National Cancer Center of Korea. RNA isolation was performed using TRIzol reagent (Invitrogen) according to the manufacturer's instructions. For this, a reverse transcription PCR system (Promega) was employed in the presence of primer sets of 5'-ACCTGTCTGCCAATCAGGAC-3'(SEQ ID NO. 3) and 5'-CCCATTCTTCTTGGAGGTCA-3'(SEQ ID NO. 4) for amplifying FSCN1, 5'-ATGGCAGACAATTTTTCGCTCC-3'(SEQ ID NO. 5) and 5'-ATGTCACCAGAAATTCC CAGTT-3'(SEQ ID NO. 6) for amplifying LGAL3, 5'-AGC-CTCGCCTTTGCCGA-3'(SEQ ID NO. 7) and 5'-CTGGT-GCCTGGGGCG-3'(SEQ ID NO. 8) for amplifying β-actin, and 5'-GGCTGCTTTTAACTCTGGTA-3'(SEQ ID NO. 9) and 5'-ACTTGATTTTGGAGGGAT CT-3'(SEQ ID NO. 10) for amplifying GAPDH (glyceraldehyde-3-phosphate dehydrogenase). PCR was conducted with Ex-taq (TaKaRa).

<1-3> Western Blotting and Immunoprecipitation

For use in Western blotting and immunoprecipitation, cell lysates were prepared in RIPA buffer containing a protease inhibitor cocktail. Immunoblotting was performed with anti-galectin-3, anti-fascin-1, anti-GSK-3β, anti-TCF-4 (Santa-Cruz), anti-GSK-3β[pS$^6$] (biosourse), anti-β-catenin and anti-lamin A/C (Cell-Signaling), and anti-β-actin (Sigma). Immunoprecipitation was performed with A/G agarose beads coated with anti-galectin-3 and anti-β-catenin. Proteins were detected by Western Blotting with anti-galectin-3, anti-β-catenin, anti-GSK-3β and anti-TCF-4. Mouse/rabbit IgG was used as a negative control.

<1-4> Construction of Galectin-3 Expression Lentiviral Vector and Infection therewith The full-length human galectin-3 gene cloned in the expression vector pcDNA3.1-NT-GFP-gal3 was amplified by PCR using a primer set of 5'-ATGGCAGACAATTTTTCGCT-3' (SEQ ID NO. 13) and 5'-TTATATCATGGTATATGAAGCACTGGT-3' (SEQ ID NO. 14). The PCR product thus obtained was cloned into pcDNA3.1-NT-GFP using the TA cloning method (Invitrogen). Such modifications caused the lenti-viral vector pLL3.7 (Addgene Inc) to overexpress LacZ, wild-type gal-3, and gal-3 S96A. pLL3.7 was constructed by PCR amplification using the following human full-length wild-type gal-3 primers having BamH1/Xho1 restriction sites; 5'-GGATCCATGGCAGACAATTTTTCGCTC-3' (SEQ ID NO. 15) and 5'-TCGAGTTATATCATGGTATAT GAAGC-3'(SEQ ID NO. 16). Galectin-3 S96A was composed of two fragments: one was amplified with a primer set of 5'-GGATCCATGGCAGACAATTTTTCGCTC-3' (SEQ ID NO. 17) and 5'-GACAGCCAGCAGCCACCGGAGCCTCACCTGCCACT-3' (SEQ ID NO. 18); the other with a primer set of 5'-TCCGGTG-GCTGCTGGCTGTCCAGAAGATGGGTAGGC-3' (SEQ ID NO. 19) and 5'-CTCGAGTTATATCATGG TATAT-GAAGC-3' (SEQ ID NO. 20). These two fragments were combined into one fragment using BamH1/Xho1 restriction enzymes. In combination with three plasmids VSVG, RSV-REV and PMDLg/pPRE, pLL 3.7 was co-transfected into 293 cells to produce lentiviral particles. The 293FT cells were transfected using Lipofectamine 2000 according to the instruction of manufacturer's. The 293FT cell cultured media were filtered using a 0.45-µm filter. Lenti virus infections of lacZ, gal-3 wild, and gal-3 S96A were performed in a media of SNU-638 cells.

<1-5> Immunocytochemistry and Immunohistochemistry

Cells cultured in chamber slides were fixed and blocked with 5% bovine serum albumin (BSA) in PBS and then incubated with primary anti-galectin-3, anti-fascin-1, anti-GSK-3β, anti-β-catenin antibodies diluted (1:200) in PBS. The cells were conjugated with the secondary antibodies labeled with FITC, Cy5 (Zymed), or Texas Red-X phalloidin (Invitrogen). The samples were treated with a mounting medium, and analyzed with a confocal microscope (Carl-Zeiss). Immunohistochemistry for galectin-3, β-catenin, and fascin-1 of gastric cancer patient tissues was performed according to the instructions, using a Vectastain ABC kit and DAB substrate kit (Vector Laboratories).

<1-6> Transfilter Migration, Wound Healing, and Invasion Assays

Transfilter migration and invasion assays were performed with 8.0-µm pore inserts in a 24-well Transwell. For this assay, MKN-28 and SNU638 cells were transfected overnight with siRNAs. Then, they were isolated and added to the upper chamber of a Transwell with 0.5 mg/mL collagen type 1 (BD Bioscience)-coated filters in migration assay. The invasion assay was performed using $\frac{1}{15}$ diluted Matrigel (BD Bioscience)-coated filters at $2\times10^4$ cells/well. RPMI 1640 supplemented with 10% fetal bovine serum and 1% antibiotics was added to the lower chamber and the cells were allowed to incubate for 20 hours. Migrating and invading cells were quantified after H&E staining. Each experiment was performed in triplicate and mean values are presented. A wound healing assay was performed according to the published protocol (Liang C C, Park A Y, Guan J L. In vitro scratch assay: a convenient and inexpensive method for analysis of cell migration in vitro. Nat Protoc 2007; 2:329-33).

<1-7> Chromatin Immunoprecipitation Assay

Chromatin immunoprecipitation assays were performed using a chIP assay kit (Upstate), according to the manufacturer's instructions. Anti-TCF4, anti-β-catenin, anti-galectin-3, and rabbit IgG were used to immunoprecipitate DNA-containing complexes. Primer was prepared with fascin-1 promoter binding sites: fascin-1 promoter (−1321), 5'-AAT-GTCCAGGAAAAGCCTCA-3' (SEQ ID NO. 11) and (−1061) 5'-CCCAATTTCATGGGACTCTG-3' (SEQ ID NO. 12), followed by performing PCR.

<1-8> Luciferase Assay

A TCF4 luciferase reporter plasmid under control of 8 TCF4 consensus was employed, with SP1 plasmids such as a 3 SP1 consensus used as a negative control. To check the effects of galectin-3 on TCF4 transcriptional activity, stable cell lines, such as LacZ, galectin-3 wild, and galectin-3 S96A-infected SNU638 cell lines, were made through the lentivirus. These cell lines together with SNU638 were transfected with 1 µg TCF4 consensus plasmid and 1 µg SP1 plasmids using Lipofectamine 2000 (Invitrogen) reagents. 30-40 hrs after the transfection, the cells were harvested, and analyzed for luciferase activity using a luciferase assay system (Promega).

<1-9> Soft Agar Growth Assay

A layer of 0.5 mL RPMI 1640 containing 0.5% agar and 5% fetal bovine serum was placed in 24-well plates. After solidification of this bottom layer, cells transfected with galectin-3 and fascin-1 siRNAs ($1.25 \times 10^4$ per well) were poured into a top layer of 0.25 mL RPMI 1640 containing 0.3% agar and 5% fetal bovine serum. Colonies were scored by microscopic examination after 3 weeks. All samples were prepared in triplicate.

Experimental Example 1

Figure 1:
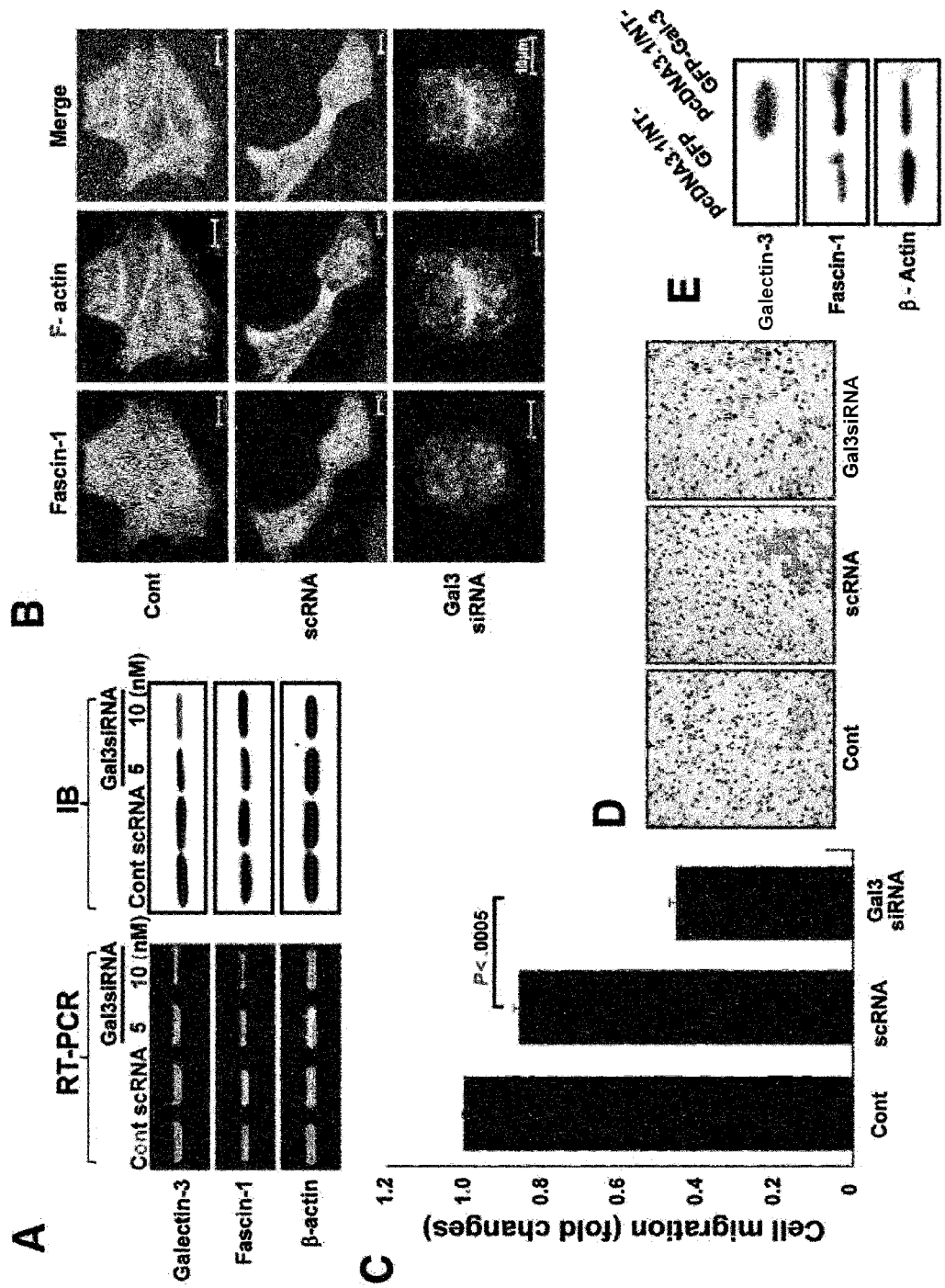
FIG. 1 shows the effect of galectin-3 silencing on the expression of fascin-1 in human gastric cancer cells. (A) mRNA and protein levels of galectin-3 and fascin-1 in human gastric cancer MKN-28 cells after transfection with scrambled siRNA (scRNA) or galectin-3 siRNA at two different concentrations (5 and 10 nmol/L). Total RNA and protein obtained from the cells harvested 48 hrs after the transfection were analyzed by RT-PCR and Western blotting. β-actin was used as a loading control. (B) Immunocytochemical analysis of scRNA or galectin-3 siRNA-transfected MKN-28 cells by DAPI (blue), anti-fascin-1 FITC (green) and anti-F-actin Texas Red (red) was detected with a confocal microscope. Bars represent a length of 10 µm. (C and D) A histogram depicting the migration of galectin-3 silenced cells. The results of the migration assay are presented with a statistical significance (P<0.0005) (C), and in cell photographs (D). (E) Expression levels of galectin-3 and fascin-1 in SNU-638 cells were determined by Western blotting after transfection with pcDNA3.1/NT-GFP-Galectin-3 and vector control of pcDNA3.1/NT-GFP. β-actin was used as a loading control.
Figure 9:
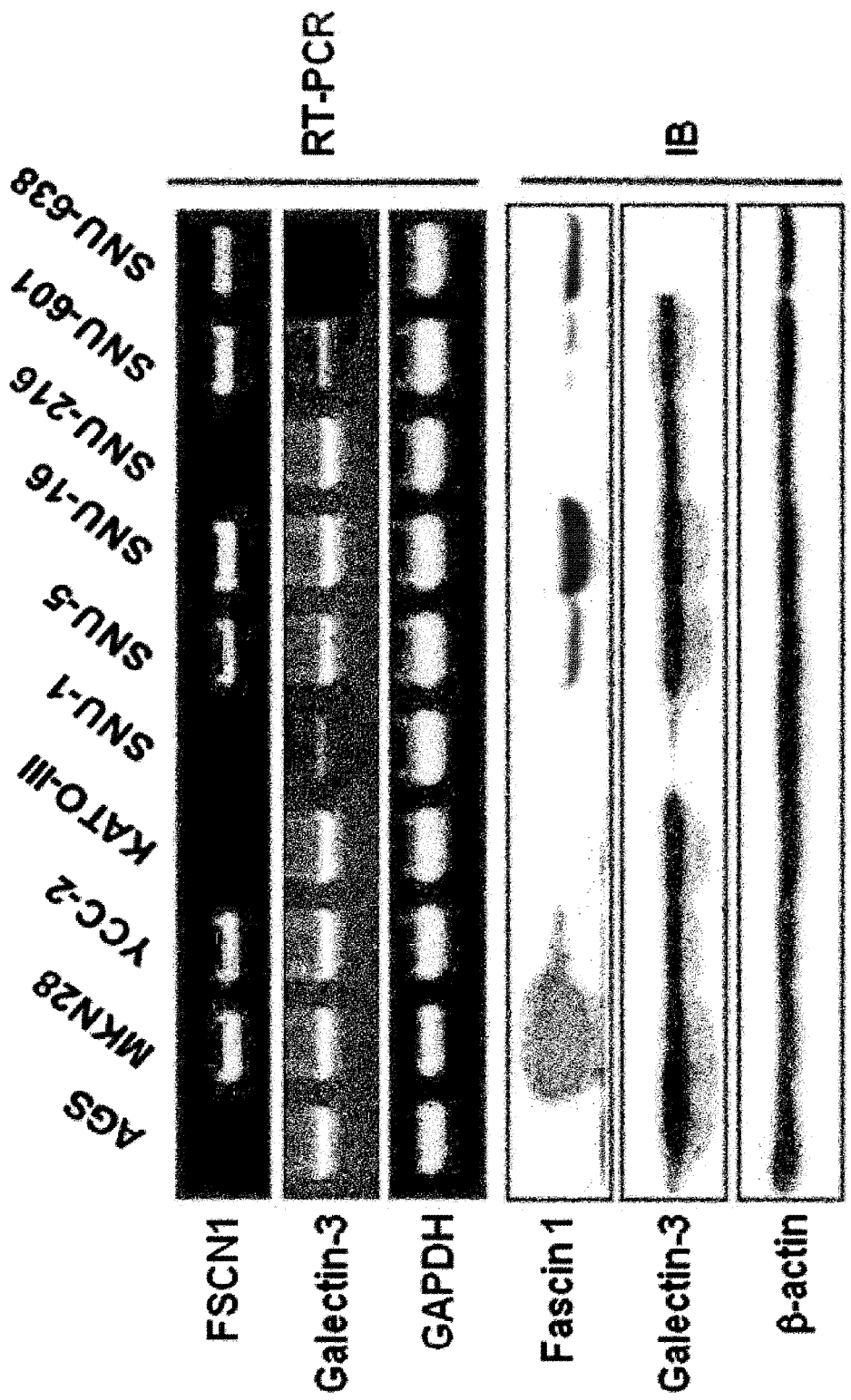
FIG. 9 shows the expression levels of mRNAs and proteins of galectin-3 and fascin-1 in 10 gastric cancer cell lines. Analyses were performed by RT-PCR and Western blotting. O-actin was used as a normalization control.

Silencing of Galectin-3 Reduces Cell Migration and Causes Changes in the Morphology of Human Gastric Cancer Cells The expression levels of galectin-3 and fascin-1 in 10 gastric cancer cell lines were determined by RT-PCR and Western blotting (FIG. 9). The expression of galectin-3 was high in 8 of 10 cell lines, and the expression of fascin-1 was high in 6 cell lines. To examine the effect of galectin-3 on fascin-1, galectin-3 was silenced with its siRNA in MKN-28 cells, which strongly express both galectin-3 and fascin-1. Galectin-3 silencing by siRNA resulted in a reduction in the expression levels of mRNAs and proteins of both galectin-3 and fascin-1 (FIG. 1A). The localization of F-actin, bundled and arranged by fascin-1, appeared at cell-cell contact areas, and at protruded edge areas in the untransfected, or scrambled siRNA (negative control) transfected, MKN-28 cells (FIG. 1B). However, fascin-1 expression diminished in the cytosol, and F-actin appeared only at cell-cell contact areas in galectin-3-silenced cells. Further, these cells became round in shape and did not have any protruding regions.

Migration assays were performed to determine the effect of galectin-3 silencing on cancer cell motility, and cells were counted (FIG. 1C), and captured by microscope (FIG. 1D). The galectin-3-silenced cells were no longer mobile, and the total number of migrated cells was reduced by almost half.

Also, the galectin-3 plasmid was transfected into SNU-638 cells. It was found that the cells did not express galectin-3 and only weakly expressed fascin-1 (FIG. 9). In contrast, increased fascin-1 expression was detected in galectin-3-overexpressing cells (FIG. 1E).

Experimental Example 2

Galectin-3 Promotes Motility of Human Gastric Cancer Cells Through Up-regulation of Fascin-1 Expression Fascin-1 siRNAs were employed to examine whether a decrease in fascin-1 expression reduces cancer cell motility. Fascin-1 siRNAs reduced fascin-1 expression in MKN-28 cells (FIG. 2A), and decreased the migration of fascin-1-silenced cells (FIG. 2B). The morphology of fascin-1-silenced cells was changed to a round shape without spikes, and F-actin appeared only in cell-cell contact areas, as happened with galectin-3-silenced cells (FIG. 2C). We also determined the effects of galectin-3 or fascin-1 silencing on cell invasion, colony formation, and wound healing as well as cell migration (FIGS. 2D to 2F). As expected, galectin-3 or fascin-1 silencing significantly reduced all of these phenomena.

Figure 3:
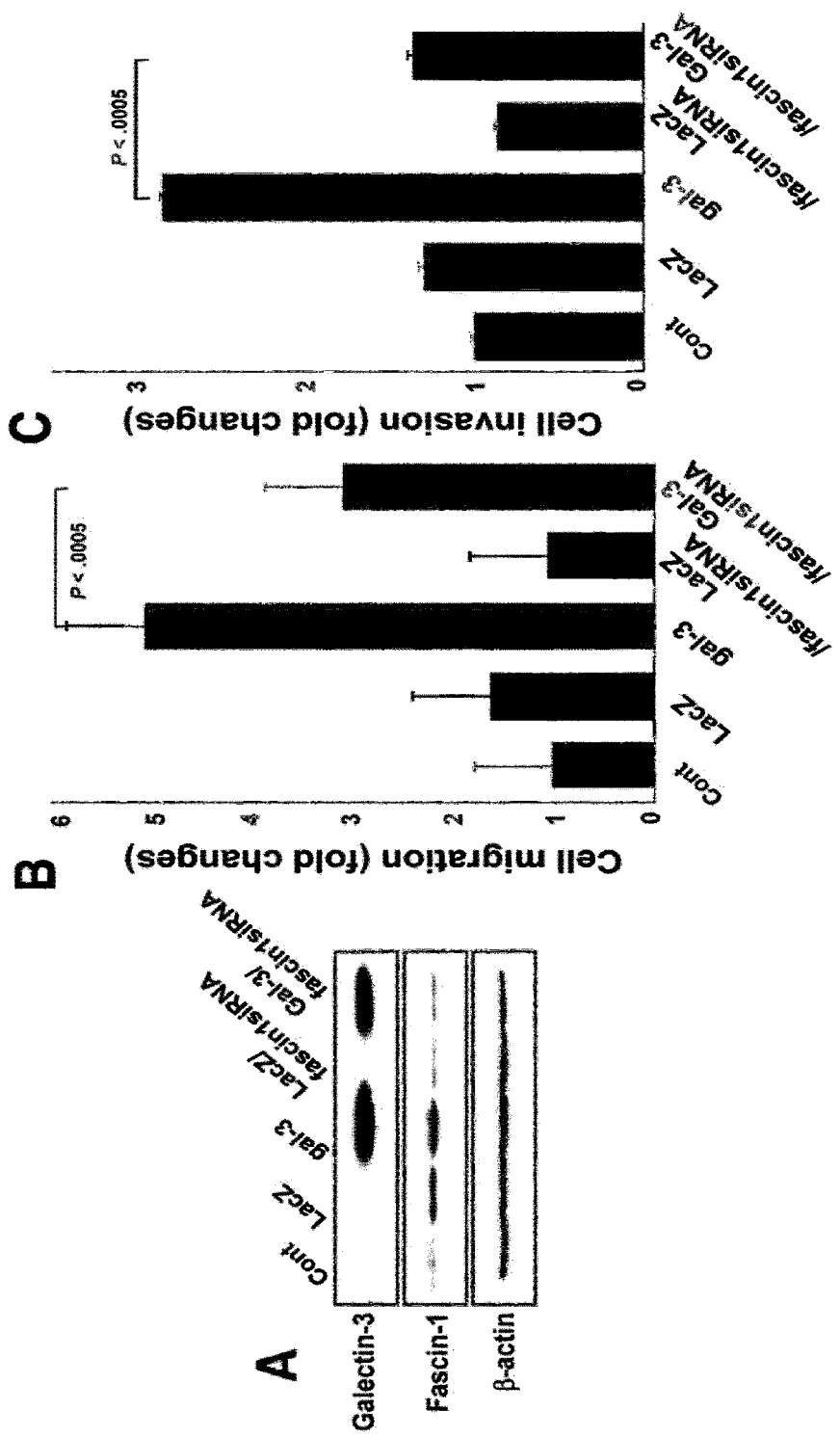
FIG. 3 shows an increase in the motility of human gastric cancer cells as a result of galectin-3 overexpression, which also up-regulates fascin-1 expression. (A) Expression levels of galectin-3 and fascin-1 were detected by Western blot analysis in SNU-638 cells which were infected with a lenti-virus containing LacZ or galectin-3 and then transfected with fascin-1 siRNA or scrambled RNA as a negative control. β-actin was used as a loading control. (B and C) These cells were analyzed by migration assay (B) and invasion assay (C), presented as histograms (P<0.0005)

An examination was made into whether galectin-3 regulates cell motility and invasion in relation to fascin-1 expression. In this regard, a galectin-3-containing lenti-virus construct was prepared and infected into SNU638 cells, and fascin-1 expression in these cells was reduced using fascin-1 siRNAs (FIG. 3). Galectin-3-overexpressing cells showed an increased level of fascin-1 protein, which was diminished by fascin-1 siRNA (FIG. 3A). Also, cell migration and invasion assays were performed on these cells. As shown in FIG. 3B, galectin-3 overexpression increased cell migration while fascin-1 silencing significantly reduced their increased migration caused by galectin-3 overexpression. An inhibitory effect of fascin-1 silencing on cell invasion by galectin-3 overexpression also was detected (FIG. 3C), but its effect was greater on cell migration. These results suggest that galectin-3 promotes gastric cancer cell motility by regulating fascin-1 expression.

Experimental Example 3

Galectin-3 Silencing Inhibits β-Catenin and TCF-4 Interaction and Reduces DNA Binding Activity of TCF-4

Figure 4:
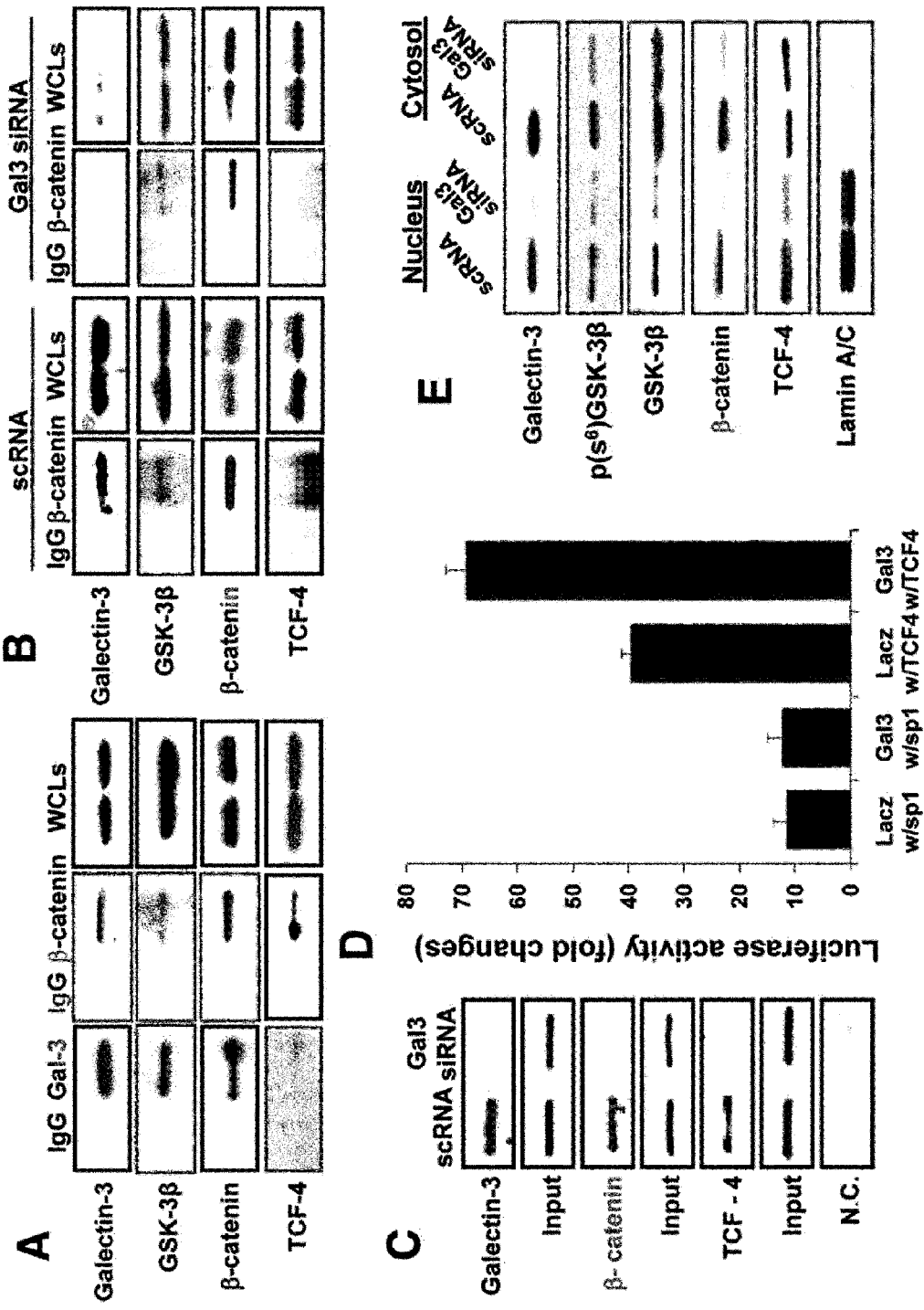
FIG. 4 shows the interaction of galectin-3 with β-catenin and TCF-4, and the reduction of DNA binding activity of TCF-4 after galectin-3 silencing in human gastric cancer cells. (A) Galectin-3 interacts with GSK-3β, β-catenin, and TCF-4 in gastric cancer cells. After immunoprecipitation, galectin-3, GSK-3β, β-catenin, and TCF-4 were detected by Western blot analysis. Whole-cell lysate was used as a positive control. (B) Interaction of GSK-3β, β-catenin, and TCF-4 in the absence of galectin-3 expression. After transfection with scrambled siRNA (scRNA) or galectin-3 siRNA of MKN-28 cells, immunoprecipitation was performed, and then galectin-3, GSK-3β, β-catenin, and TCF-4 were detected by Western blot analysis. Whole-cell lysates were used as a positive control. (C) Chromatin immunoprecipitation assay was performed as described in the Materials and Methods of the Example section. Total genomic DNA on an input lane was used as a control for the PCR reaction. (D) Luciferase activity of TCF4 in lacZ and galectin-3 overexpressing cells. Luciferase assay was performed as described in the Example section. A construct of SP1 consensus was used as a negative control. (E) Protein levels of galectin-3, phosphorylated GSK-3β, GSK-3β, β-catenin, and TCF-4 were detected in the nuclear and cytosol fractions of MKN-28 cells with or without galectin-3 siRNA treatment. Lamin A/C was used as a nuclear fraction control.

To determine how galectin-3 regulates fascin-1 expression, we surveyed its fascin-1 promoter regions (FIG. 10A). There are several kinds of transcriptional factor binding domains, such as nuclear factor-κB, TCF-4, and CREB. Some reports have it that the expression of fascin-1 is regulated by Wnt/β-catenin signaling and that galectin-3 interacts with β-catenin in colon cancer cells. To confirm this interaction in gastric cancer, after immunoprecipitation by anti-galectin-3 or anti-β-catenin antibodies, galectin-3, GSK-3β, β-catenin, and TCF-4 were detected by Western blotting (FIG. 4A). As a result, galectin-3 showed interaction with all of them: GSK-3β, β-catenin, and TCF-4. However, galectin-3 silencing diminished the interaction between β-catenin and TCF-4, implicating the loss of DNA binding activity of TCF-4 (FIG. 4B). The interaction between GSK-3β and β-catenin was weakened in the absence of galectin-3 expression.

Accordingly, an examination was made of the DNA binding activity of β-catenin and TCF-4 with or without galectin-3 by a ChIP assay (FIG. 3C). β-catenin and TCF-4 were observed to bind to the promoter regions of fascin-1 in the presence of galectin-3, but they lost their binding activity without galectin-3. The transcriptional activity of TCF-4 by galectin-3 was also analyzed (FIG. 4D). After the transfection of genes containing TCF4 binding motif in luciferase promoter into LacZ or galectin-3 overexpressing SNU-638 cells, the transcriptional activity of TCF-4 was significantly increased in the cells overexpressing galectin-3. These results imply that galectin-3 promotes interaction between β-catenin and TCF-4 and thus enhances the DNA binding affinity of TCF-4 to initiate fascin-1 transcription.

Experimental Test

Figure 5:
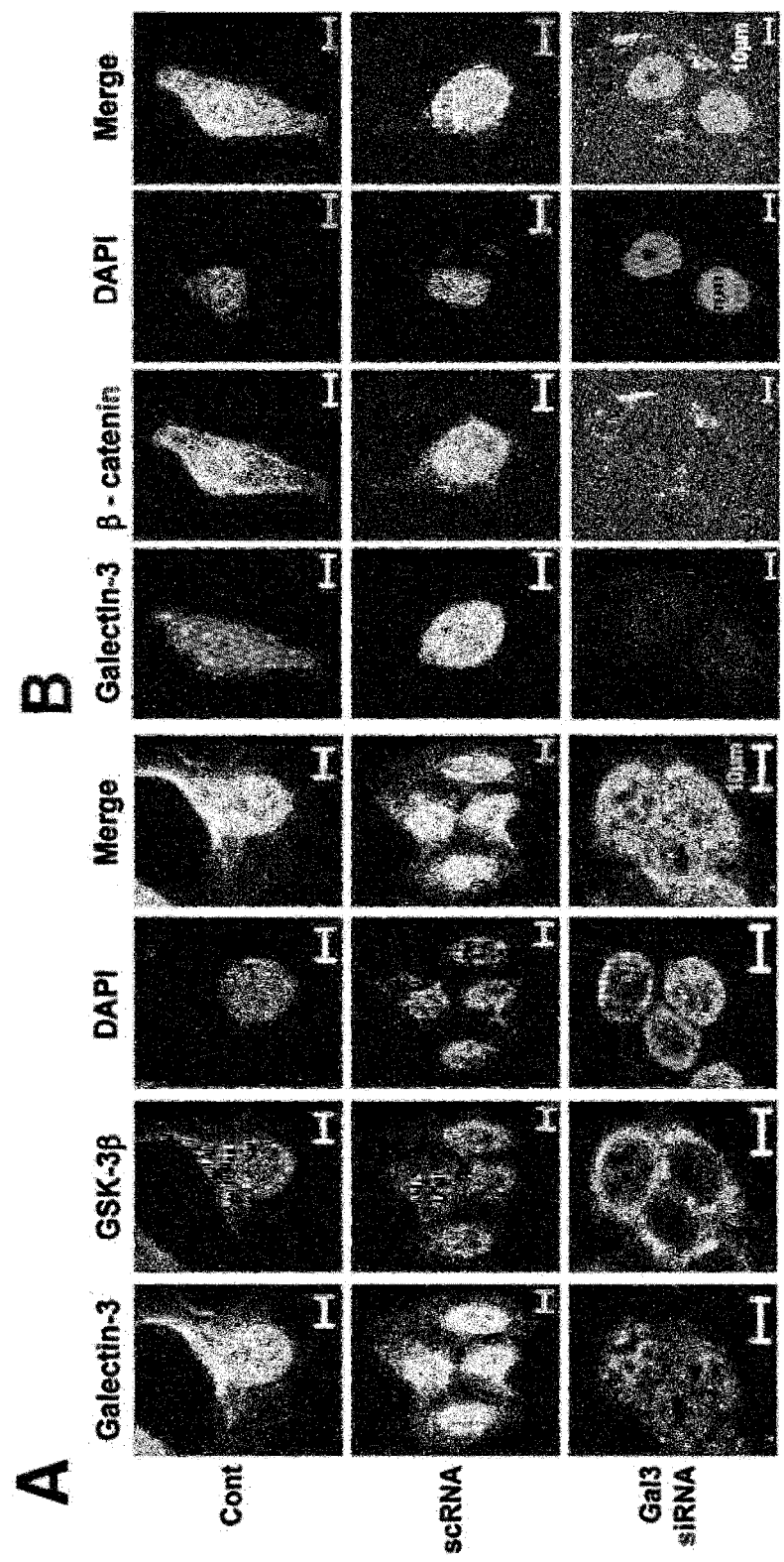
FIG. 5 shows the effect of galectin-3 silencing on the nuclear localization and the stability of β-catenin and GSK-3β in human gastric cancer cells. (A and B) Cellular localization of GSK-3β and β-catenin in galectin-3-silenced cells as analyzed by immunocytochemistry in which anti-galectin-3 fluorescein isothiocyanate (green) and anti-GSK-3β cy5 (red) (A), anti-β-catenin fluorescein isothiocyanate (green) and anti-galectin-3 cy5 (red) (B) were used under a confocal microscope. DAPI was used to figure out the nucleus (blue). Bars represent a 10 µm length.

Galectin-3 Silencing Reduces the Nuclear Localization and the Stability of β-Catenin The expression levels and localizations of GSK-3β, β-catenin, and TCF-4 after galectin-3 silencing were determined by Western blotting (FIG. 4E) and immunocytochemistry (FIGS. 5A and B). In control cells, galectin-3 was observed to colocalize with GSK-3β and β-catenin/TCF-4 in both the cytosol and in the nucleus. In galectin-3-absent cells, however, the level of phosphorylated GSK-3β and β-catenin decreased in both the nucleus and the cytosol (FIG. 4E). Interestingly, GSK-3β was located in both cytosol and the nucleus, together with galectin-3 and β-catenin. In contrast, in the absence of galectin-3, GSK-3β was located only in cytosol, and β-catenin was not detected either in the nucleus or cytosol (FIGS. 5A and B). These results suggest that galectin-3 binds with GSK-3β and β-catenin and go into the nucleus, but without galectin-3, GSK-3β exists in the cytosol with β-catenin and phosphorylates and degrades it.

Experimental Example 5

Galectin-3 Mutated at Amino Acid 96 Cannot Induce the Expression of Fascin-1 in Human Gastric Cancer Cells To further prove that galectin-3 regulates the DNA binding activity of β-catenin/TCF-4 as a result of interacting with GSK-3β, a lenti-viral construct with galectin-3 mutated at amino acid 96 (serine to alanine) were prepared and infected into SNU638 cells (FIG. 6A). Serine 92 and serine 96 on galectin-3 were expected to bind GSK-3β (FIG. 10A). Galectin-3 was detected both in the wild-type and mutated (S96A) lenti-viral construct-infected cells (FIG. 6A). Interestingly, fascin-1 expression was detected in wild-type galectin-3-infected cells, but not in the mutated galectin-3-infected cells. Increased phosphorylation of GSK-3β and expression of β-catenin also was detected in the wild-type, but not in the mutated type. TCF4 transcriptional activity in S96A-mutated galectin-3-overexpressing cells was determined by TOP flash assay (FIG. 6B). The galectin-3 wild-type-overexpressing cells increased in TCF4 transcriptional activity. However, less activity was detected in S96A-mutated galectin-3-overexpressing cells.

These results strongly support the conclusion that the interaction of galectin-3 with GSK-3β regulates the stability of β-catenin and the expression of fascin-1.

Experimental Example 6

Figure 7:
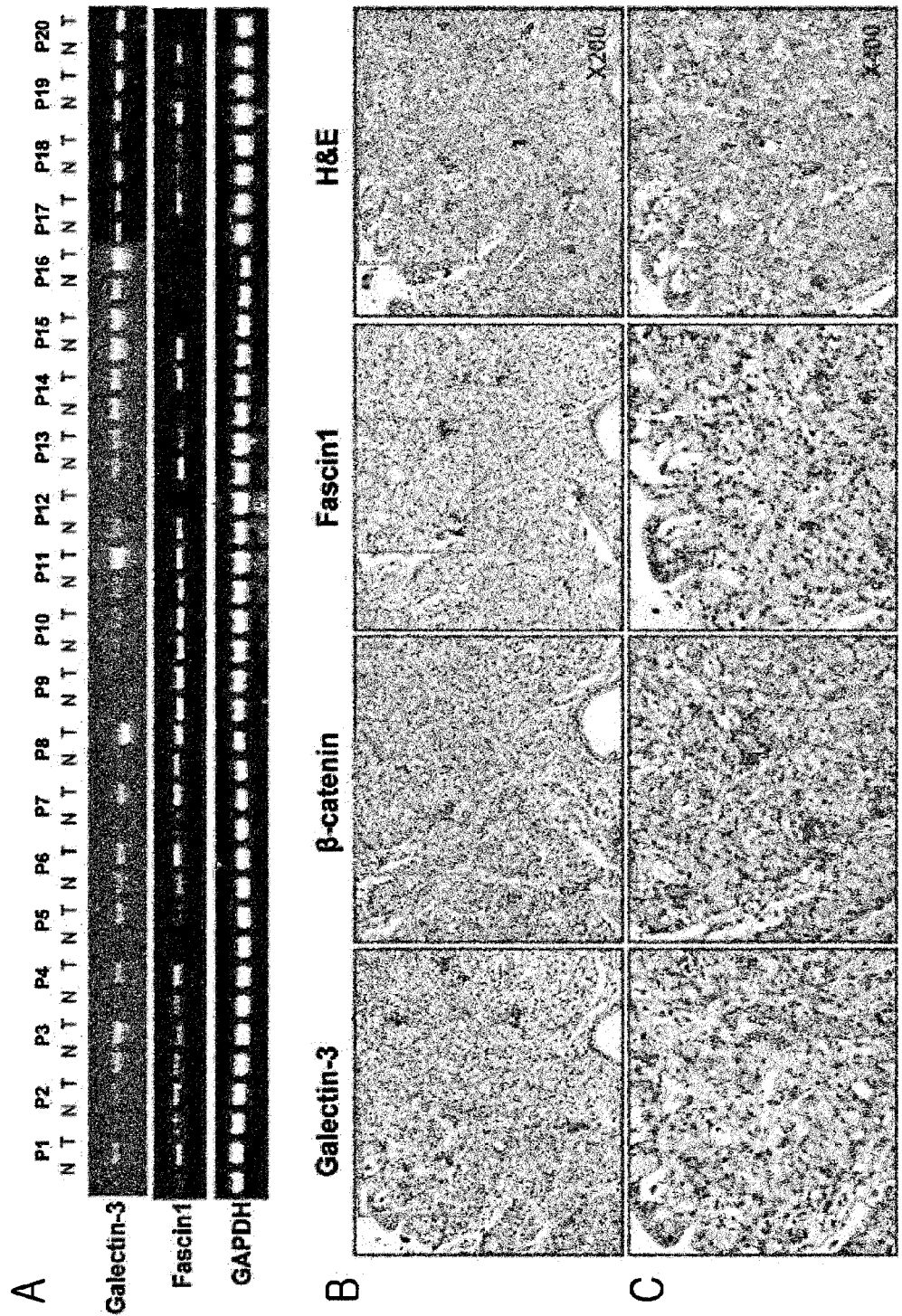
FIG. 7 shows a clinical correlation between galectin-3, β-catenin, and fascin-1 levels in gastric cancer patients. (A) mRNA levels of galectin-3 and fascin-1 in gastric cancer patients as measured by RT-PCR analysis. Malignant and normal tissue pairs were obtained from each of 20 gastric patients, and PCR was performed as described in the Materials and Methods section. GAPDH was used as a normalization control. (B and C) Expression of galectin-3, β-catenin, and fascin-1 in gastric cancer tissues as detected by immunohistochemical staining (brown) with H&E under a fluorescence microscope. Magnification: (B) ×200; (C) ×400.

Clinical Correlation between Galectin-3, β-Catenin, and Fascin-1 Levels in Gastric Cancer Patients First, the expression levels of galectin-3 and fascin-1 in 20 gastric cancer patients in the National Cancer Center of Korea were examined. Total RNA of normal and cancerous tissue from these patients was prepared and RT-PCR was performed (FIG. 7A). Quantification was made using an image analyzer (Table 1).

The expression levels of both galectin-3 and fascin-1 were higher in cancerous tissue than in normal tissue. An increase in galectin-3 and fascin-1 expression levels was detected, respectively, in 73.7% (14 of 19) and 66.7% (12 of 18) of cases. Moreover, 71.4% of galectin-3-positive patients were also fascin-1 positive. Only two patients showed fascin-1 expression in the absence of galectin-3. However, we could not show any correlation between metastatic profiles and the positivity of these genes because these patients were diagnosed mostly in the early stages without there being any metastasis.

TABLE 1

| Expression | Ratio | Percentage |
|---|---|---|
| galectin-3 | 14/19 | 73.7 |
| Fascin-1 in galactin-3 | 12/18 | 66.7 |
| Fascin-1 in galactin-3 expression | 10/14 | 71.4 |

Immunohistochemical staining showed the overexpression and co-localization of galectin-3 and β-catenin in gastric cancer tissues (FIG. 7B). They were localized in both the cytosol and the nucleus (FIG. 7C). Fascin-1 also was expressed in the same area, but mainly in the cell membranes (FIG. 7C). These results suggest that fascin-1 expression significantly correlates with galactin-3 and β-catenin in gastric cancer patients.

As described hitherto, the screening method of the present invention facilitates the detection of a possible chemotherapeutic agent which can decrease the motility of tumor cells by down-regulating the expression of galectin-3 and fascin-1, and preferably allows a broad spectrum of chemotherapeutic agents that work against gastric cancer to be searched through.

The chemotherapeutic agents based on the present invention inhibit the activity of galectin-3 and fascin-1 or promote the degradation thereof to interfere with interaction between galectin-3 and GSK-3β, thus preventing cancer metastasis and making a great contribution to the survival rate of cancer patients.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An in vitro method for screening a compound capable of inhibiting the binding of GSK-3β with galectin-3 and down-regulating the expression of fascin-1 in gastric cancer cells, comprising:
    a) treating gastric cancer cells with a candidate agent;
    b) measuring (i) binding of galectin-3 with glycogen synthetase kinase-3β (GSK-3β) in the nucleus of the gastric cancer cell treated with the candidate agent, and (ii) expression level of fascin-1 in the gastric cancer cells treated with the candidate agent; and
    c) identifying a candidate agent as the compound when the binding of galectin-3 and GSK-3β in the nucleus measured in step b)(i), and the expression level of fascin-1 measured in step b)(ii) are reduced in the gastric cancer cells as compared to the gastric cancer cells before treatment with the candidate agent,
    wherein the candidate agent is a galectin-3 siRNA.

2. The method of claim 1, wherein the expression level of fascin-1 is measured by an mRNA or protein level of fascin-1.

3. The method of claim 1, wherein the compound reduces the binding of GSK-3β with galectin-3 at position 92 to 96 of galectin-3 as set forth in SEQ ID NO.:21.

4. The method of claim 1, wherein the gastric cancer cells are metastatic gastric cancer cells.

5. The method of claim 1, wherein the treated gastric cancer cells further show reduced motility.

* * * * *